(12) United States Patent
Paradis

(10) Patent No.: US 10,722,423 B2
(45) Date of Patent: Jul. 28, 2020

(54) APPLICATOR FOR APPLYING A COSMETIC TREATMENT PRODUCT TO THE SKIN OR THE LIPS

(71) Applicant: Line Paradis, Dubai (AE)

(72) Inventor: Line Paradis, Dubai (AE)

( * ) Notice: Subject to any disclaimer, the term of this patent is extended or adjusted under 35 U.S.C. 154(b) by 0 days.

(21) Appl. No.: 15/622,137

(22) Filed: Jun. 14, 2017

(65) Prior Publication Data

US 2018/0311104 A1 Nov. 1, 2018

(30) Foreign Application Priority Data

Apr. 28, 2017 (FR) ...................................... 17 53774

(51) Int. Cl.
| | | |
|---|---|---|
| *A61H 7/00* | (2006.01) | |
| *A61M 35/00* | (2006.01) | |
| *A61M 37/00* | (2006.01) | |
| *A61B 17/34* | (2006.01) | |

(52) U.S. Cl.
CPC ............ *A61H 7/001* (2013.01); *A61M 35/003* (2013.01); *A61M 37/0076* (2013.01); *A61H 2201/123* (2013.01)

(58) Field of Classification Search
CPC ................. A61H 7/00; A61B 17/3417
See application file for complete search history.

(56) References Cited

U.S. PATENT DOCUMENTS

| | | | | |
|---|---|---|---|---|
| 2004/0116953 A1* | 6/2004 | Dixon | ............... | A61M 37/0076 606/186 |
| 2013/0197560 A1* | 8/2013 | Cheng | .................. | A61B 17/205 606/186 |

FOREIGN PATENT DOCUMENTS

| | | |
|---|---|---|
| DE | 102011120366 A1 | 6/2013 |
| EP | 2011539 A1 | 1/2009 |
| KR | 20130058843 A | 6/2013 |
| WO | 2005110395 A1 | 11/2005 |
| WO | 2007011788 A2 | 1/2007 |
| WO | 2017210017 A1 | 12/2017 |

OTHER PUBLICATIONS

International Search Report from PCT Application No. PCT/FR2018/052608, dated Feb. 5, 2019.

* cited by examiner

*Primary Examiner* — Tatyana Zalukaeva
*Assistant Examiner* — Sara A Sass
(74) *Attorney, Agent, or Firm* — Workman Nydegger

(57) ABSTRACT

The disclosure provides an applicator for applying a cosmetic treatment product to the skin or the lips, the applicator comprising at least:
an application portion comprising a bundle of needles for applying the cosmetic treatment product and extending along a longitudinal axis, the bundle of needles comprising at least one first set of needles having a distribution that is square in cross-section relative to the longitudinal axis; and
a linear drive device connected to the application portion and configured to constrain the bundle of needles to perform reciprocating motion along the longitudinal axis.

23 Claims, 2 Drawing Sheets

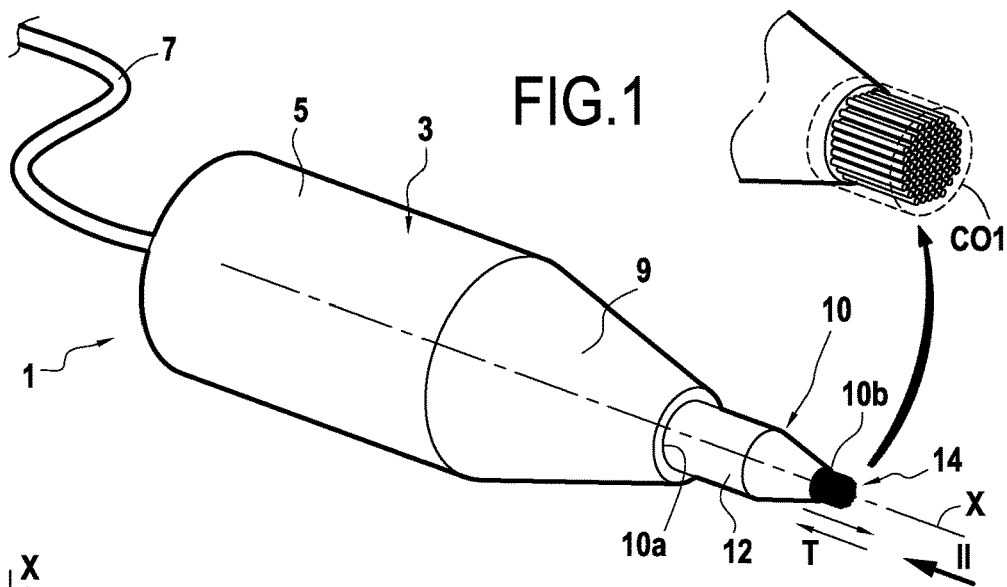
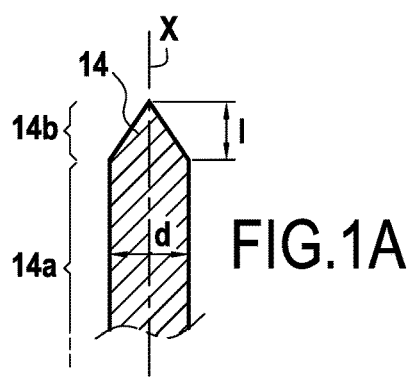
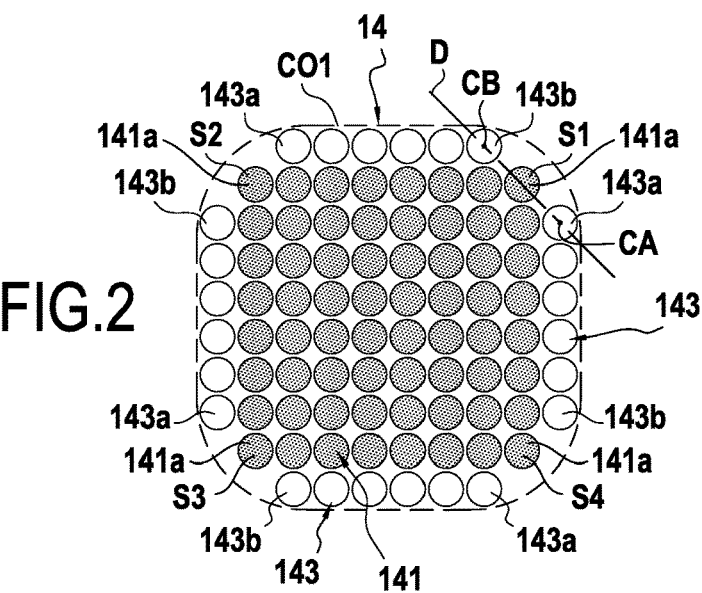
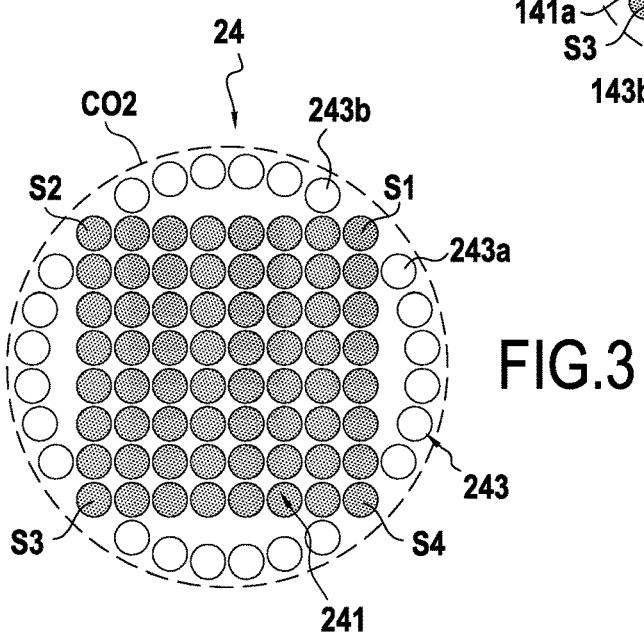

APPLICATOR FOR APPLYING A COSMETIC TREATMENT PRODUCT TO THE SKIN OR THE LIPS

BACKGROUND

There currently exist several types of method that can be implemented in order to remove a tattoo from the skin.

In particular, use may be made of chemical methods in which a liquid tattoo removal composition is injected, through the skin, into the dermis where it is tattooed. That technique uses a system that is somewhat similar to the system used for tattooing, comprising a plurality of needles suitable for puncturing the skin in order to inject the tattoo removal composition. Known tattoo removal compositions make it possible to dissolve the pigments of the tattoo and cause them to be rejected at the surface of the skin.

However, those tattoo removal techniques present an invasive character in the sense that they require the skin to be punctured during treatment. Such techniques cause discomfort to the subject undergoing the tattoo removal treatment and may lead to the subsequent appearance of unsightly scars.

That problem, which is linked to puncturing of the surface being treated by the application device, may also be encountered with other cosmetic treatments, for example, with permanent makeup.

SUMMARY

The present inventor has thus recognized that there exists a need to provide a device that serves to perform effective cosmetic treatment of the skin or the lips, while limiting, or even avoiding, puncturing of the surface being treated. To this end, embodiments of the disclosure provide an applicator for applying a cosmetic treatment product to the skin or the lips, the applicator comprising at least:

- an application portion comprising a bundle of needles for applying the cosmetic treatment product and extending along a longitudinal axis, the bundle of needles comprising at least one first set of needles arranged in a square in cross-section relative to the longitudinal axis; and
- a linear drive device connected to the application portion and configured to drive the bundle of needles with reciprocating motion along the longitudinal axis.

For reasons of brevity, the term "cross-section relative to the longitudinal axis" is, unless otherwise stated, referred to below as "cross-section".

The applicator of the disclosure serves to perform cosmetic treatment that is effective while also reducing the risk of puncturing the surface of the skin or the lips being treated. In particular, embodiments of the disclosure are remarkable due to the presence of the first set of needles arranged in a square. This disposition leads to equal distribution of the pressure applied by the needles on the surface being treated, which reduces the risk of puncturing the surface, while enabling effective cosmetic treatment to be performed.

In an embodiment, the bundle of needles further comprises a second set of needles situated around the first set of needles and defining an outline for the bundle of needles that presents a rounded shape in cross-section relative to the longitudinal axis.

In order to minimize the risk of puncturing in use, the user preferably imposes an angle close to 90° between the longitudinal axis along which the needles move and the surface being treated. However, depending on the user's dexterity, said angle may be maintained to a greater or lesser extent during treatment. Using such a bundle of needles with a rounded outline makes it possible to limit any risk of puncturing the surface, and does so even if the user does not maintain the above-mentioned angle close to the value of 90°. Such a bundle thus serves to introduce a large amount of tolerance in terms of possible sloping of the longitudinal axis relative to the surface during application. The second set of needles this serves to "protect" the surface being treated from the sharp corners of the square, even with the longitudinal axis sloping considerably relative to the surface being treated.

In particular, the square defined by the first set of needles presents a plurality of corners, and each corner is situated between two consecutive needles of the second set of needles.

As described in more detail below, in cross-section, the rounded outline may present a shape that is square with rounded corners or a shape that is circular.

In a variant, the first set of needles defines an outline for the bundle of needles that presents a shape that is square in cross-section relative to the longitudinal axis.

Such a bundle applicator presenting a square outline is advantageously used to impose an angle close to 90° between the longitudinal axis and the surface being treated.

When the outline is square in shape and as described in more detail below, the bundle of needles may comprise only the first set of needles. In a variant, the bundle of needles may further comprise a third set of needles, the first set of needles being situated around the third set of needles.

In an embodiment, the number of needles forming the bundle of needles lies in the range 81 to 132.

Such a characteristic makes it possible to apply the cosmetic product on the surface being treated with optimum pressure, and consequently to obtain optimum efficiency for the cosmetic treatment being performed.

In an embodiment, the needles forming the bundle of needles are short-taper needles.

The term "short-taper needle" should be understood as referring to a needle having a taper that extends along a length that is not greater than 2 millimeters (mm).

In an embodiment, the needles forming the bundle of needles present a diameter lying in the range 0.25 mm to 0.40 mm.

Unless otherwise stated, the term "diameter" should be understood as the greatest transverse dimension measured perpendicularly to the longitudinal axis X.

By way of example, the diameter may lie in the range 0.25 mm to 0.35 mm or in the range 0.30 mm to 0.40 mm. In particular, the diameter may be substantially equal to 0.30 mm or to 0.35 mm.

In an embodiment, the applicator is in the form of a handpiece.

In a second aspect, the disclosure also provides a cosmetic treatment method implementing an applicator as described above, the method comprising at least the following step:

applying to a surface of the skin or the lips a cosmetic treatment product present on the bundle of needles, the bundle of needles being driven with reciprocating motion along the longitudinal axis during application.

In an embodiment, the longitudinal axis forms an angle lying in the range 450 to 135° relative to the surface treated during application.

The above-mentioned applicators having a bundle of needles with a rounded outline may advantageously be used over this entire range of angles during treatment. However, during treatment, it is advantageous to maintain an angle lying in the range 70° to 110° between the longitudinal axis and the surface being treated when using a bundle having a square outline, so as to minimize any risk of puncturing the skin.

The applicator may be used in various cosmetic applications. In particular, the applicator can be used to apply a cosmetic product that is for migrating through the surface being treated. It is then possible to perform dermapigmentation or tattoo removal treatments. Thus, the treatment method may be a tattoo removal method for removing a tattoo from the skin or the lips. In a variant, the treatment method may be a method of applying permanent makeup to the skin or the lips.

BRIEF DESCRIPTION OF THE DRAWINGS

Other characteristics and advantages of the disclosure appear from the following description of particular embodiments of the disclosure, given by way of non-limiting example and with reference to the accompanying drawings, in which:

FIG. 1 is a diagrammatic and fragmentary view of an example of an applicator of the disclosure;

FIG. 1A is a diagram showing a short-taper needle, taken in isolation, forming part of the bundle of needles used in the applicator of FIG. 1;

FIG. 2 is a view in cross-section of the bundle of needles of the applicator of FIG. 1;

FIG. 3 is a view in cross-section of a variant of the bundle of needles that may be used in the context of the disclosure;

DETAILED DESCRIPTION

Figure 4:
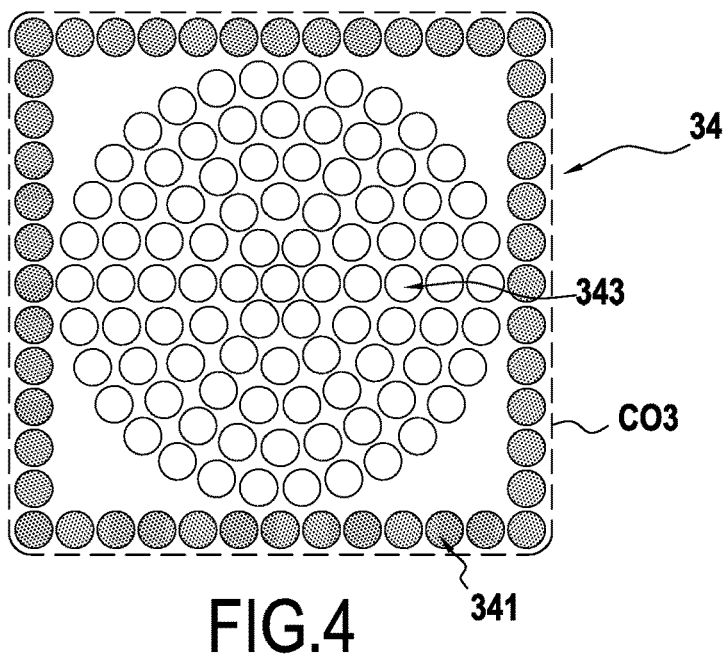
FIG. 4 is a view in cross-section of a variant of another variant of the bundle of needles that may be used in the context of the disclosure.

FIG. 1 shows an example of an applicator 1 according to embodiments of the disclosure. The applicator 1 is presented in the form of a handpiece. The applicator 1 comprises a body 3 presenting a proximal portion 5 housing a linear drive device. The drive device is configured to impart reciprocating motion to the bundle 14 of needles. The drive device constitutes a motorized device that is not original per se. The drive device is connected to an electricity generator (not shown) by means of the electric cable 7. The body 3 further presents a distal portion 9 forming a grip portion. As an example of a body 3 enclosing a drive device that is suitable for use in the context of the disclosure, mention can be made of the "Dermo Power Pen" commercial device (Linda Paradis).

The applicator 1 further comprises an endpiece 10 connected to the body 3. The endpiece 10 comprises a shell 12 surrounding the bundle 14 of needles. The bundle 14 of needles extends inside the envelope 12. The needles forming the bundle 14 of needles are secured to one another and are thus held in a predetermined position. The bundle 14 extends along a longitudinal axis X. In this embodiment, the assembly constituted by the envelope 12 and by the bundle 14 of needles is in the form of a cartridge that is connected to the body 3. The envelope 12 thus defines a portion 10a for fastening the endpiece 10, which portion is inserted in a housing made in the distal portion 9 of the body 3 so as to fasten the endpiece 10 to the body 3.

The bundle 14 of needles forms the application portion of the applicator 1. The needles 14 are thus designed to be put into contact with the cosmetic composition so as to apply it on the surface being treated. The distal portion 10b of the endpiece 10 is defined by the bundle 14 of needles. The bundle 14 of needles projects beyond the envelope 12.

Naturally, the needles 14 are sterile before use of the applicator 1. The needles 14 are single use needles. The needles 14 may be made of a metal material, such as stainless steel. The diameter d of each of the needles 14 may lie in the range 0.25 millimeters (mm) to 0.40 mm, and for example may be substantially equal to 0.3 mm or to 0.35 mm. As shown in FIG. 1A, the needles 14 may comprise a portion 14a of constant diameter extended by a tapering portion 14b of decreasing diameter. The tapering portion 14b defines the taper of the needle, the portion 14b is designed to come into contact with the surface being treated. Short-taper needles 14 (needles that are known per se) may be used. Such needles 14 present a taper 14b having a length l that is not greater than 2 mm.

During actuation of the drive device, the needles 14 perform reciprocating motion along the axis X. The reciprocating motion is represented by two arrows T in FIGS. 1 and 6. The reciprocating motion constitutes an alternating forward and backwards movement in translation along the axis X. When the drive device is actuated, the bundle 14 of needles moves as a whole with reciprocating motion along the axis X.

As mentioned above, embodiments of the disclosure are remarkable in that the bundle of needles comprises at least one set of needles having a distribution in cross-section that is square, with the use of such a set of needles limiting any risk of puncturing the surface being treated. Various possible shapes for the bundle of needles are described with reference to FIGS. 2 to 5.

FIG. 2 shows the bundle 14 of needles used in the applicator of FIG. 1 seen in cross-section relative to the axis X. The cross-section may be taken perpendicularly to the axis X.

The bundle 14 of needles comprises a first set 141 of needles that forms a square when the bundle 14 is observed in cross-section. The square presents a plurality of corners S1-S4. The needles forming the first set 141 of needles are in contact with one another.

In the embodiment in FIG. 2, the bundle 14 of needles further comprises a second set 143 of needles situated around a first set 141 of needles. Each corner S1-S4 is situated between two consecutive needles 143a and 143b of the second set 143 of needles. The expression "two consecutive needles of the second set of needles" refers to two needles of the second set 143 of needles that are consecutive when going around the first set 141 of needles. Thus, each needle 141a of the first set situated at a corner S1-S4 is situated between two consecutive needles 143a and 143b of the second set. When the bundle 14 is observed in cross-section, each corner needle 141a is situated on the straight line D connecting the centers CA and CB of the two consecutive needles 143a and 143b situated on either side of the needle 141a under consideration.

In the example shown in FIGS. 1 and 2, the outline CO1 of the bundle 14 is defined by the needles of the second set 143 of needles. The outline CO1 extends around the needles of the second set 143. The outline CO1 constitutes a surface of tubular shape. The outline CO1 defines the bundle 14 of needles. The outline CO1 constitutes the outer surface of the bundle 14 of needles. The outline CO1 extends along the axis X. The bundle 14 of needles is present inside the outline CO1.

In this embodiment, in cross-section, the outline CO1 is in the shape of a square with rounded corners. The presence of the needles of the second set 143 rounds the shape of the corners S1-S4 of the square defined by the first set 141 of needles. As mentioned above, the presence of the second set 143 makes it possible, in use, to introduce a large amount of tolerance in terms of possible inclination of the bundle 14 relative to the surface being treated, while limiting any risk of puncturing said surface. The needles of the second assembly 143 thus make it possible to "protect" the surface being treated from the sharp corners S1-S4 in the event of the bundle being strongly inclined during use.

In the particular shape illustrated in FIG. 2, the needles of the second set 143 are situated along each side of the square formed by the needles of the first set 141. A single row of needles of the second set 143 is present along each side of the square formed by the needles of the first set 141. In each of the rows, the needles 143 are in alignment parallel to the side of the square situated facing the row under consideration.

The example of a bundle 14 shown in this embodiment comprises 88 needles distributed as 64 needles (8×8 square) for the first set 141 and 24 needles (6×4) for the second set 143. In a variant, and by way of example, a bundle having the same shape but comprising 132 needles (10×10+8×4) could be used. These values of 88 and 132 needles make it possible to obtain maximum treatment efficiency for the shape, however the values are given by way of non-limiting preference.

FIG. 3 shows a variant of a bundle 24 of needles having an outline that also presents a rounded shape in cross-section.

The bundle 24 of needles comprises a first set 241 of needles having a distribution in cross-section that is square, as well as a second set 243 of needles situated around the first set 241.

The second set 243 of needles provides the bundle 24 of needles with an outline CO2 of rounded shape in cross-section. Unlike the example of FIG. 2, in this embodiment the outline CO2 is of cross-section that is circular, and not square with rounded corners.

In the same manner as in the example of FIG. 2, each corner S1 is situated between two consecutive needles 243a and 243b of the second set 243. The bundle 24 of needles shown in FIG. 3 is, in cross-section, in the shape of a square inscribed in a circle.

In the same manner as for the bundle 14 of FIG. 2, the bundle 24 may advantageously be formed of 88 needles (first set 241: 64 needles, and second set 243: 24 needles), or it may be formed of 132 needles (first set 241: 100 needles, and second set 243: 32 needles).

Each of the examples of bundles 14 and 24 that are described above with reference to FIGS. 2 and 3 presents an outline of rounded shape in cross-section.

However, the disclosure is not limited to this possibility; bundles having in cross-section an outline of different shape are described below with reference to FIGS. 4 and 5.

In the embodiment in FIG. 4, the bundle 34 comprises a first set 341 of needles having a distribution in cross-section that is square. The bundle 34 further comprises a third set 343 of needles, the first set 341 of needles being situated around the third set 343 of needles. In this embodiment, the third set 343 has a distribution in cross-section that is circular.

In this example, the outline CO3 of the bundle 34 is defined by the first set 341 of needles and presents a cross-section of square shape. The outline CO3 extends around the needles of the first set 341.

The bundle of needles 34 shown in FIG. 4 presents, in cross-section, the shape of a circle inscribed in a square.

Figure 5:
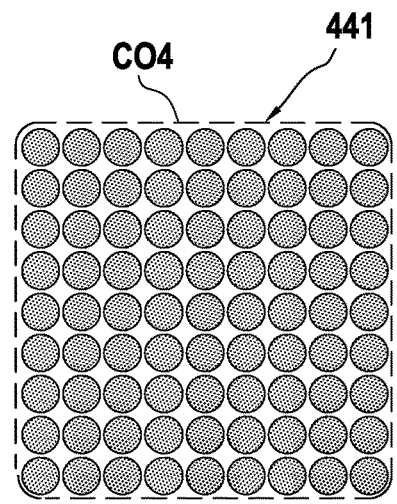
FIG. 5 is a view in cross-section of a variant of another variant of the bundle of needles that may be used in the context of the disclosure.

FIG. 5 shows the example in which the bundle of needles 441 is formed only by the first set 441 of needles. The outline CO4 of the bundle 441 thus presents, in cross-section, a square shape. In this event, the bundle 441 may comprise 81 (9×9 square) or 100 (10×10 square) needles.

Various possible shapes for the bundle of needles have been described. Performing an implementation of a cosmetic treatment according to embodiments of the disclosure is described below with reference to FIG. 6.

Figure 6:
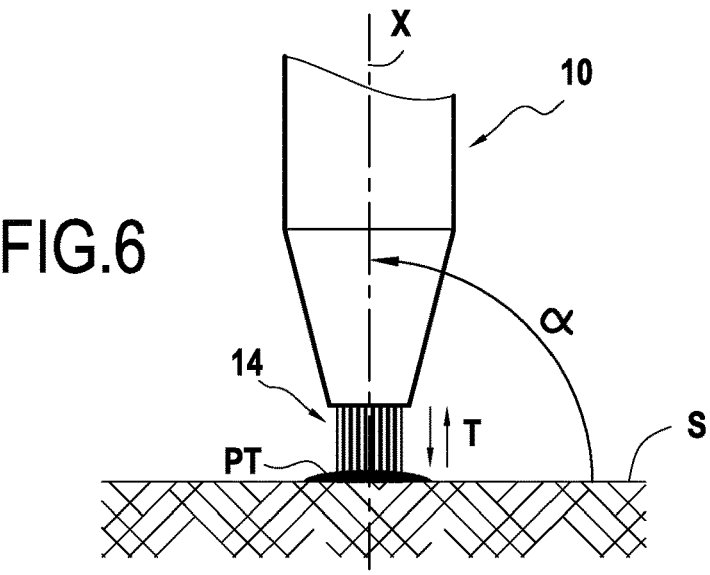
FIG. 6 is a diagrammatic and fragmentary view showing an implementation of a cosmetic treatment method of the disclosure being performed.

FIG. 6 shows the implementation of a cosmetic treatment of a surface S of the skin or the lips by means of an applicator 1 according to embodiments of the disclosure. In particular, the surface S can be an area of the face or the body.

Initially, a cosmetic treatment product PT is applied on the bundle 14 of needles. The product PT may be in the liquid state. The product PT may be configured to migrate through the surface S. The alternating pressure produced by the reciprocating motion of the bundle 14 of needles contributes to facilitating migration. The product PT serves to perform the cosmetic treatment at the dermis. The applicator 1 serves to perform dermapigmentation treatment on the skin or the lips or tattoo removal treatment on the skin or the lips.

For tattoo removal, the product PT is a liquid tattoo removal composition suitable for migrating through the surface S. Such a liquid composition makes it possible to extract tattoo ink out from the surface S in order to perform tattoo removal. By way of example of a utilizable tattoo removal composition, mention may be made of the "Tattoo Remoov™" commercial composition (Linda Paradis).

For dermapigmentation treatment, permanent makeup of the skin or the lips may be performed by using a permanent makeup product PT suitable for migrating through the surface S. Such a product may be an inorganic pigment-based product, and it also constitutes a known product.

In order to perform application, the needles 14 impregnated with the product PT move with a reciprocating motion along the axis X. The bundle 14 moves transversely relative to the surface treated during application. The bundle 14 of needles has a piston effect that facilitates penetration of the product. In the embodiment in FIG. 6, during application the axis X is held at an angle α that is substantially equal to 90° relative to the surface S. The configuration makes it possible to limit as far as possible any risk of puncturing the surface S. However, if a bundle with a rounded outline is used, such as the bundle 14 of FIG. 2 or the bundle 24 of FIG. 3, satisfactory results can be obtained over the range 45° to 135° for the angle α.

The expression "lying in the range . . . to . . . " should be understood as including the bounds.

Throughout the description, including the claims, the term "comprising a" should be understood as being synonymous with "comprising at least one" unless otherwise stated. In addition, any range set forth in the description, including the claims should be understood as including its end value(s) unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances.

The invention claimed is:

1. An applicator for applying a cosmetic treatment product to skin or lips, the applicator comprising at least:
   an application portion comprising a bundle of needles for applying the cosmetic treatment product and extending along a longitudinal axis, the bundle of needles comprising at least one first set of needles, the needles of the first set of needles collectively being arranged in a square in cross-section relative to the longitudinal axis; and
   a linear drive device connected to the application portion and configured to drive the bundle of needles with reciprocating motion along the longitudinal axis,
   wherein the bundle of needles further comprises a second set of needles situated around the first set of needles and defining an outline for the bundle of needles that presents a rounded shape in cross-section relative to the longitudinal axis, and
   wherein the bundle of needles includes:
   88 needles distributed as 64 needles in the first set of needles and 24 needles in the second set of needles, or
   132 needles distributed as 100 needles in the first set of needles and 32 needles in the second set of needles;
   wherein the rounded shape of the outline of the bundle of needles limits risk of puncturing a surface of the skin or the lips and
   permits a large tolerance in a range of an angle between the longitudinal axis of the bundle of needles and the surface of the skin or of the lips.

2. The applicator according to claim 1, wherein the square defined by the first set of needles presents a plurality of corners, and wherein each corner is situated between two consecutive needles of the second set of needles.

3. The applicator according to claim 1, wherein the total number of needles forming the bundle of needles lies in the range 88 to 132.

4. The applicator according to claim 1, wherein the needles forming the bundle of needles are short-taper needles having a length that is 2 mm or less.

5. The applicator according to claim 1, wherein the needles forming the bundle of needles present a diameter lying in the range 0.25 mm to 0.40 mm.

6. The applicator according to claim 1, wherein the applicator is in the form of a handpiece.

7. A cosmetic treatment method implementing an applicator according to claim 1, the method comprising at least the following step:
   applying to a surface of the skin or the lips a cosmetic treatment product present on the bundle of needles, the bundle of needles being driven with reciprocating motion along the longitudinal axis during application.

8. The method according to claim 7, wherein the method is a tattoo removal method for removing a tattoo from the skin or the lips or a method of applying permanent makeup to the skin or the lips.

9. The applicator according to claim 1, wherein the bundle of needles includes 88 needles distributed as 64 needles in the first set of needles and 24 needles in the second set of needles.

10. The applicator according to claim 9, wherein the second set of needles includes at least four sub-sets of needles, each of the needles of the four sub-sets being respectively arranged linearly.

11. The applicator according to claim 9, wherein the needles of the first set of needles are arranged with centers of the respective needles aligned along a plurality of lines, and the needles of the second set of needles are arranged with centers of the respective needles aligned along a non-linear curve.

12. The applicator according to claim 9, wherein the needles of the first set of needles are arranged with centers of the respective needles aligned along a plurality of lines, and the needles of the second set of needles are arranged with centers of the respective needles aligned along a circle.

13. The applicator according to claim 9, wherein needles of a first sub-set of the second set of needles are arranged closer to the first set of needles than are needles of a second sub-set of the second set of needles to needles of the first set of needles, the needles of the first sub-set being provided closer to the corner of the square than the needles of the second sub-set are to the corners of the square, such that a gap is provided between the needles of the second sub-set and the needles of the first set of needles between the corners of the square.

14. The applicator according to claim 9, wherein a single row of needles is present along each side of the square formed by the needles of the first set.

15. The applicator according to claim 1, wherein the bundle of needles includes 132 needles distributed as 100 needles in the first set of needles and 32 needles in the second set of needles.

16. applicator according to claim 15, wherein the second set of needles includes at least four sub-sets of needles, each of the needles of the four sub-sets being respectively arranged linearly.

17. The applicator according to claim 15, wherein the needles of the first set of needles are arranged with centers of the respective needles aligned along a plurality of lines, and the needles of the second set of needles are arranged with centers of the respective needles aligned along a non-linear curve.

18. The applicator according to claim 15, wherein the needles of the first set of needles are arranged with centers of the respective needles aligned along a plurality of lines, and the needles of the second set of needles are arranged with centers of the respective needles aligned along a circle.

19. The applicator according to claim 15 wherein needles of a first sub-set of the second set of needles are arranged closer to the first set of needles than are needles of a second sub-set of the second set of needles to needles of the first set of needles, the needles of the first sub-set being provided closer to the corner of the square than the needles of the second sub-set are to the corners of the square, such that a gap is provided between the needles of the second sub-set and the needles of the first set of needles between the corners of the square.

20. The applicator according to claim 15, wherein a single row of needles is present along each side of the square formed by the needles of the first set.

21. An applicator for applying a cosmetic treatment product to skin or lips, the applicator comprising at least:
- an application portion comprising a bundle of needles for applying the cosmetic treatment product and extending along a longitudinal axis, the bundle of needles comprising at least one first set of needles, the needles of the first set of needles collectively being arranged in a square in cross-section relative to the longitudinal axis; and
- a linear drive device connected to the application portion and configured to drive the bundle of needles with reciprocating motion along the longitudinal axis,
- wherein the bundle of needles further comprises a second set of needles situated around the first set of needles and defining an outline for the bundle of needles that presents a rounded shape in cross-section relative to the longitudinal axis, and
- wherein the bundle of needles consists of 88 needles distributed as 64 needles in the first set of needles and 24 needles in the second set of needles;
- wherein the rounded shape of the outline of the bundle of needles limits risk of puncturing a surface of the skin or the lips and
- permits a large tolerance in a range of an angle between the longitudinal axis of the bundle of needles and the surface of the skin or of the lips.

22. An applicator for applying a cosmetic treatment product to skin or lips, the applicator comprising at least:
- an application portion comprising a bundle of needles for applying the cosmetic treatment product and extending along a longitudinal axis, the bundle of needles comprising at least one first set of needles, the needles of the first set of needles collectively being arranged in a square in cross-section relative to the longitudinal axis; and
- a linear drive device connected to the application portion and configured to drive the bundle of needles with reciprocating motion along the longitudinal axis,
- wherein the bundle of needles further comprises a second set of needles situated around the first set of needles and defining an outline for the bundle of needles that presents a rounded shape in cross-section relative to the longitudinal axis, and
- wherein the bundle of needles consists of 132 needles distributed as 100 needles in the first set of needles and 32 needles in the second set of needles;
- wherein the rounded shape of the outline of the bundle of needles limits risk of puncturing a surface of the skin or the lips and
- permits a large tolerance in a range of an angle between the longitudinal axis of the bundle of needles and the surface of the skin or of the lips.

23. An applicator for applying a cosmetic treatment product to skin or lips, the applicator comprising at least:
- an application portion comprising a bundle of needles for applying the cosmetic treatment product and extending along a longitudinal axis, the bundle of needles comprising at least one first set of needles,
- wherein the bundle of needles further comprises a second set of needles situated around the first set of needles and defining an outline for the bundle of needles that presents a rounded shape in cross-section relative to the longitudinal axis, and
- wherein the bundle of needles includes 88 or 132 needles;
- wherein the rounded shape of the outline of the bundle of needles limits risk of puncturing a surface of the skin or the lips and
- permits a large tolerance in a range of an angle between the longitudinal axis of the bundle of needles and the surface of the skin or of the lips.

* * * * *